United States Patent [19]

Lee, Jr.

[11] Patent Number: 5,008,533

[45] Date of Patent: Apr. 16, 1991

[54] HIGH SPEED FIBER OPTIC CONTAINER INSPECTION APPARATUS AND METHOD

[75] Inventor: Harry W. Lee, Jr., Bon Air, Va.

[73] Assignee: Reynolds Metals Company, Richmond, Va.

[21] Appl. No.: 471,586

[22] Filed: Jan. 29, 1990

[51] Int. Cl.⁵ .......................................... G01N 9/04
[52] U.S. Cl. ................................ 250/223 B; 209/588
[58] Field of Search .................... 250/223 R, 223 B; 356/240; 209/588

[56] References Cited

U.S. PATENT DOCUMENTS

| | | | |
|---|---|---|---|
| 3,411,009 | 11/1968 | Ford et al. | 250/223 B |
| 3,963,918 | 6/1976 | Jensen et al. | 250/223 B |
| 4,241,256 | 12/1980 | Tagaya et al. | 356/240 |
| 4,276,467 | 6/1981 | Dubberly et al. | 250/223 B |
| 4,335,960 | 6/1982 | Ashcroft et al. | 250/223 B |

Primary Examiner—David C. Nelms
Assistant Examiner—K. Shami
Attorney, Agent, or Firm—Alan T. McDonald

[57] ABSTRACT

An apparatus and method for automatically inspecting containers at an increased rate is characterized by simultaneous inspection of adjacent containers by a plurality of photosensors. Containers are moved in series order along a prescribed path through an inspection area. Exterior surfaces of containers are illuminated; openings in the container bodies permit light to be transmitted to a photosensor through a viewing window in an opaque disk which shields unwanted light from the sensor. Photosensors are arranged to receive light in parallel overlapping paths. Optical units including lens and optic fiber bundles direct light from successively tested containers to different sensing paths. In an alternative embodiment, the disk has a split window configuration permitting successively tested containers to be detected by alternate sensors.

18 Claims, 5 Drawing Sheets

HIGH SPEED FIBER OPTIC CONTAINER INSPECTION APPARATUS AND METHOD

TECHNICAL FIELD

The present invention relates generally to the inspection or testing of containers and, more particularly, to photo-optically sensing defects in containers using a source of radiation, and a plurality of photosensors.

BACKGROUND ART

During the manufacture of metal cans, container bodies are inspected and tested for openings in the bottom and side wall surfaces or seams prior to completion of the fabrication process. Such defects may occur in the side or bottom areas or at the top flange areas of the containers.

Conventionally, an apparatus capable of handling a large number of can bodies transfers them at high speed through an inspection area in which defects are found. FIG. 1A depicts the conveyance path of the containers. From the infeed area 10, container bodies are advanced to be detected at station 20. The bodies are further conveyed to a discharge area 30 for either rejection of faulty containers or for advancement for further processing. Conventional apparatuses of this nature are described in U.S. Pat. No. 3,750,877 to Cvacho et al. and U.S. Pat. No. 4,305,816 to Flood et al. Cans are inserted in a continuously rotating carrier, which cooperates with a conveyance mechanism, for transfer to the inspection area. Ejection of the cans after inspection to a rejection chute is effected by a vacuum actuator if a fault determination has been made.

The inspection is performed by a photoelectric device, including a photosensor, mounted at a fixed, stationary location on the apparatus. A circular opening in the device permits light to be sensed. Cans are rotatively moved through a housing wherein the external surfaces of the cans are illuminated. The cans are uniformly positioned in the carrier at a given radial distance from the axis of rotation and oriented horizontally with their axes in parallel with the carrier axis of rotation. An opaque disk, containing a plurality of circular windows, is mounted on the carrier for rotation therewith. The windows are smaller in diameter than the cans to be inspected. During rotation of the carrier, cans are successively urged to be in contact with the disk. The open top portion of each can is aligned with, and surrounds, a window of the disk.

At the inspection area the opaque disk, positioned between the exteriorly illuminated cans and the photoelectric device, shields the latter from unwanted light. As the carrier rotates, the cans, aligned with the disk windows, successively come into registration with the opening in the photoelectric device. The disk windows serve as viewing ports for discerning passage of light through openings in the can bodies.

FIG. 1B illustrates the prior art relationship at the inspection area. The disk 1, shown in broken section, rotates in the clockwise direction about axis 2 as represented by the arrow. Windows 3 in the disk are evenly distributed along the disk at a radial distance 4. Cans, held in pockets (not shown) in the carrier and in contact with the disk, are shown having circumferences 5 which are concentric with the plate disk windows 3. Light seals, indicated at 7, are provided between pockets. The window 3 serves as a can viewing port for the opening 6 of a single stationary light sensor device. This device is responsive to light transmitted from the light source through any opening in a faulty can and the viewing port as the can passes through the optical path. In such case a signal is produced causing actuation of a compressed air device (not shown) to eject the can into a defect chute (also not shown) at the appropriate point in the travel path.

In the above described prior art apparatus the speed at which the cans can be processed is limited by the capability of the single sensor to respond to each inspection. For example, a typical arrangement would provide cans spaced at 30° increments on an 18 inch diameter circle. The cans would then be spaced 4.7 inches apart with a viewing port area of approximately 3 square inches. At a feed rate of 2000 cans per minute, the light sensor has 7.6 mil. sec. to view the inside of the can. This rate taxes the reliability of the sensor. While the inspection rate can be increased by reducing the spacing between cans, there must be room enough to permit illumination of all exterior surfaces.

A drawback of the conventional device is that it cannot distinguish the location of a fault. The detector is responsive to light from wherever the source. It would be useful to determine, for example, whether there are consistent faults in the container top flange area, as opposed to occurrences of random holes in the sheet material or fractures at the bottom; such information would indicate the need for investigation of the fabrication process.

DISCLOSURE OF THE INVENTION

Accordingly, one object of the invention is to provide an apparatus and method for inspecting containers at a high rate of speed in a smooth and efficient manner.

Another object of the invention is to provide a container testing apparatus wherein individual containers are viewed for a longer period at higher feed rates than heretofore possible to permit summing or averaging light intensity rather than instantaneous sensing.

A further object of the invention is to provide a method and apparatus for inspecting containers whereby containers can be viewed through the largest possible opening while extending the viewing time.

Another object of the invention is to provide a container inspection apparatus and method which can discriminate between a flange leak defect and an opening at the side or bottom of a container.

The above noted objects are attained by providing a plurality of light sensing units. Each unit contains a light sensor such as a photo-multiplier located within a stationary housing. The housing has an end panel with an aperture shaped in the form of a slot. The slot is elongated to be in registration with the path of travel of a can to be tested for a distance significantly greater than the diameter of the viewing window of the disk aperture. The remaining inside surfaces of the housing form a highly reflective channel to ensure that light from the can entering the channel at any point along the slot will be directed to and detected by the photo sensor.

The slots of the plurality of sensor housings are arcuately shaped and positioned in overlapping spaced relationship with each other in parallel with the path of travel of the test containers. The disk window configuration is modified and may cooperate with light directing optic fiber bundles so that adjacent containers are inspected by different sensors during overlapping time periods. Since inspection of a plurality of test containers is conducted simultaneously, each container is inspected during a longer extent of travel than that of the conventional device. The feed rate of the containers is greatly increased while the viewing time for each inspection is also increased. Bundles of optic fibers can be arranged so that light emanating from the peripheral, or flange area, can be distinguished from light originating from the center area, the latter corresponding to a defect in the bottom or side of the container.

Still other objects and advantages of the present invention will become readily apparent to those skilled in the art from the following detailed description. As will be realized, the invention is capable of other and different embodiments, and its several details are capable of modifications in various obvious respects, all without departing from the invention.

BEST MODE FOR CARRYING OUT THE INVENTION

Figure 1A:
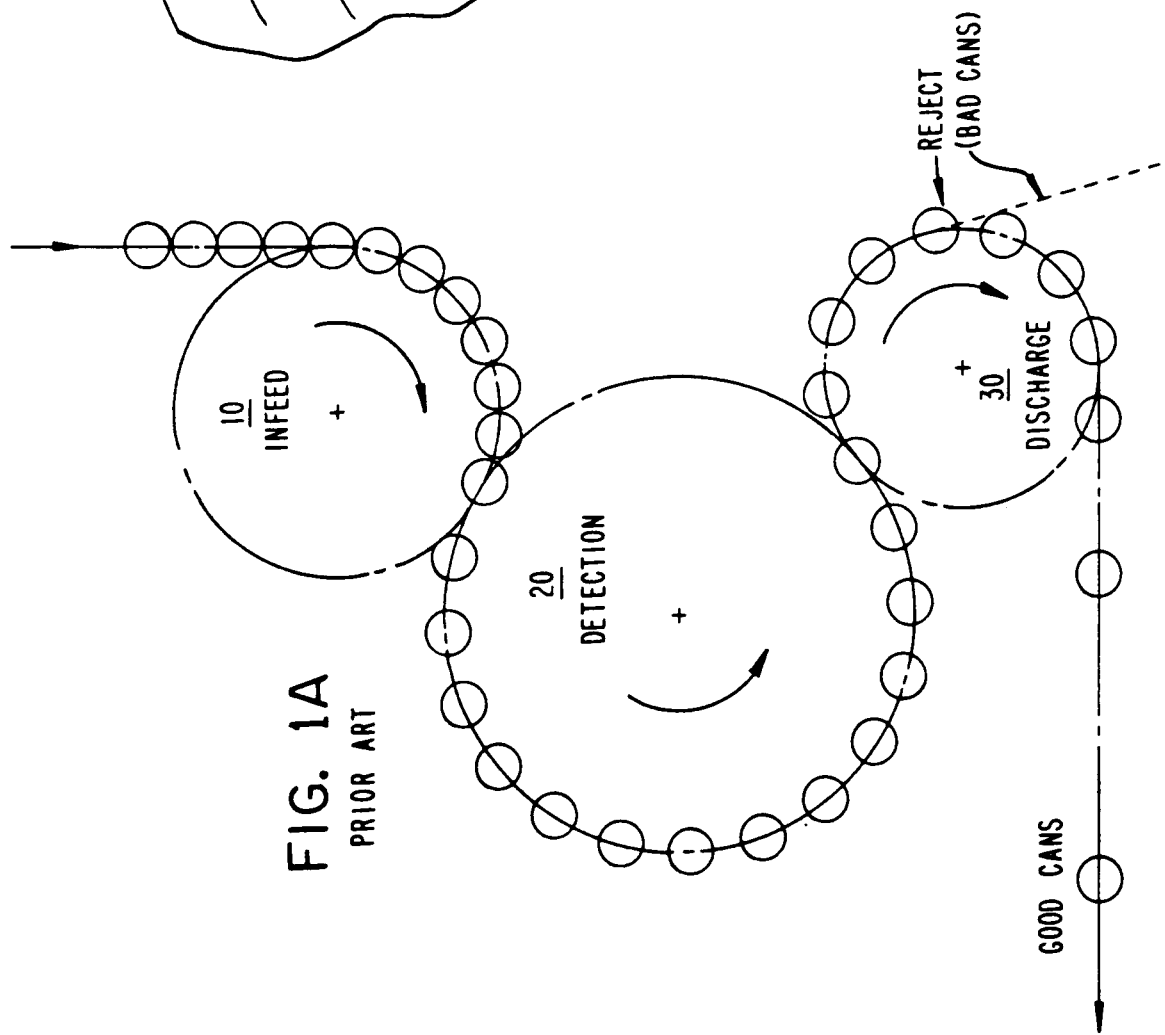
FIG. 1A is a representation of a conventional container conveying arrangement.
Figure 1B:
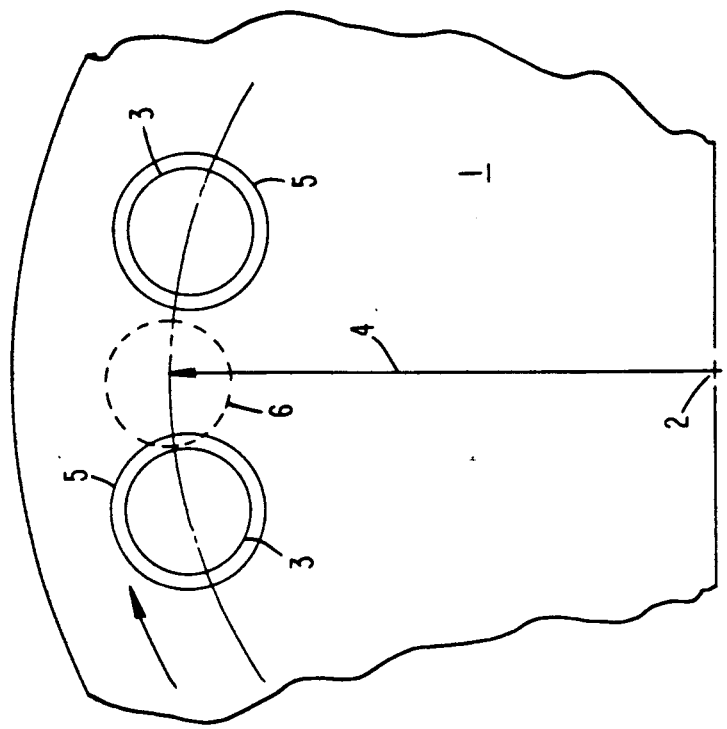
FIG. 1B shows the relationship among test containers, viewing windows and sensor at an inspection area of a container testing apparatus in accordance with the prior art.
Figure 2:
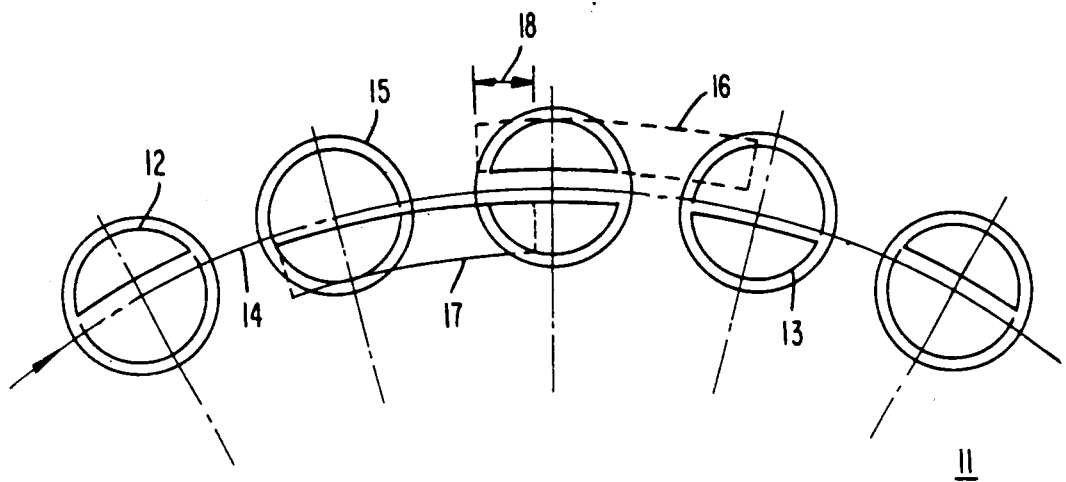
FIG. 2 is a front view of one embodiment of a container testing apparatus in accordance with the invention and shows, at an inspection area, successive chord shaped windows disposed on alternating sides of the center of container top portions in relationship with two light detecting units.

The invention is based in part on the concept that simultaneous inspection of adjacent containers on the conveying portion of a testing apparatus during overlapping time periods permits a faster rate of inspection while individual containers are viewed for longer periods. FIG. 2 illustrates one embodiment of this concept.

A partial view of disk 11 is shown in relationship to containers 15. The containers are urged to be in contact with the disk and the arrangement rotates in the clockwise direction as indicated by the arrows. Circumferential line 14, for purpose of illustration, separates the cans along their diameters into upper and lower sections. Viewing windows are provided in the disk in the form of chord shaped holes 12 and 13. The holes successively alternate on either side of line 14, the holes 12 located on the upper side of the line while the holes 13 are disposed on the lower side.

Two stationary detection units, having apertures schematically indicated by dotted line blocks 16 and 17, are provided for sensing light transmitted through the viewing windows. Aperture 16, positioned in alignment with the path of travel of the upper sections, receives light passed through upper windows 12. Aperture 17, placed below line 14, receives light passed through lower windows 13. Reflective channels within the sensor housings direct light passing through the apertures to the sensing photocells.

As a consequence of this split window arrangement, each test object is viewed for a significantly greater portion of travel than is possible with a single sensor. This result is enabled with the simultaneous sensing of adjacent containers in the area 18 in which the sensing apertures overlap. However, the sensors view the containers through off-center windows. This may be a disadvantage at times as the sensor may be more sensitive to holes on the window side than the other side of the container.

Figure 3:
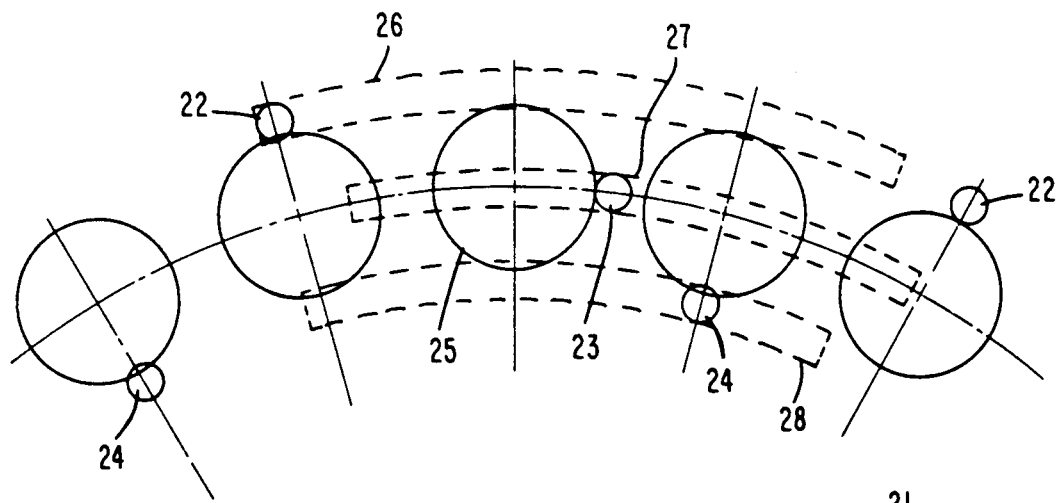
FIG. 3 is a front view of another embodiment of a container testing apparatus in accordance with the invention showing the relationship of three light detecting units at an inspection area.
Figure 4:
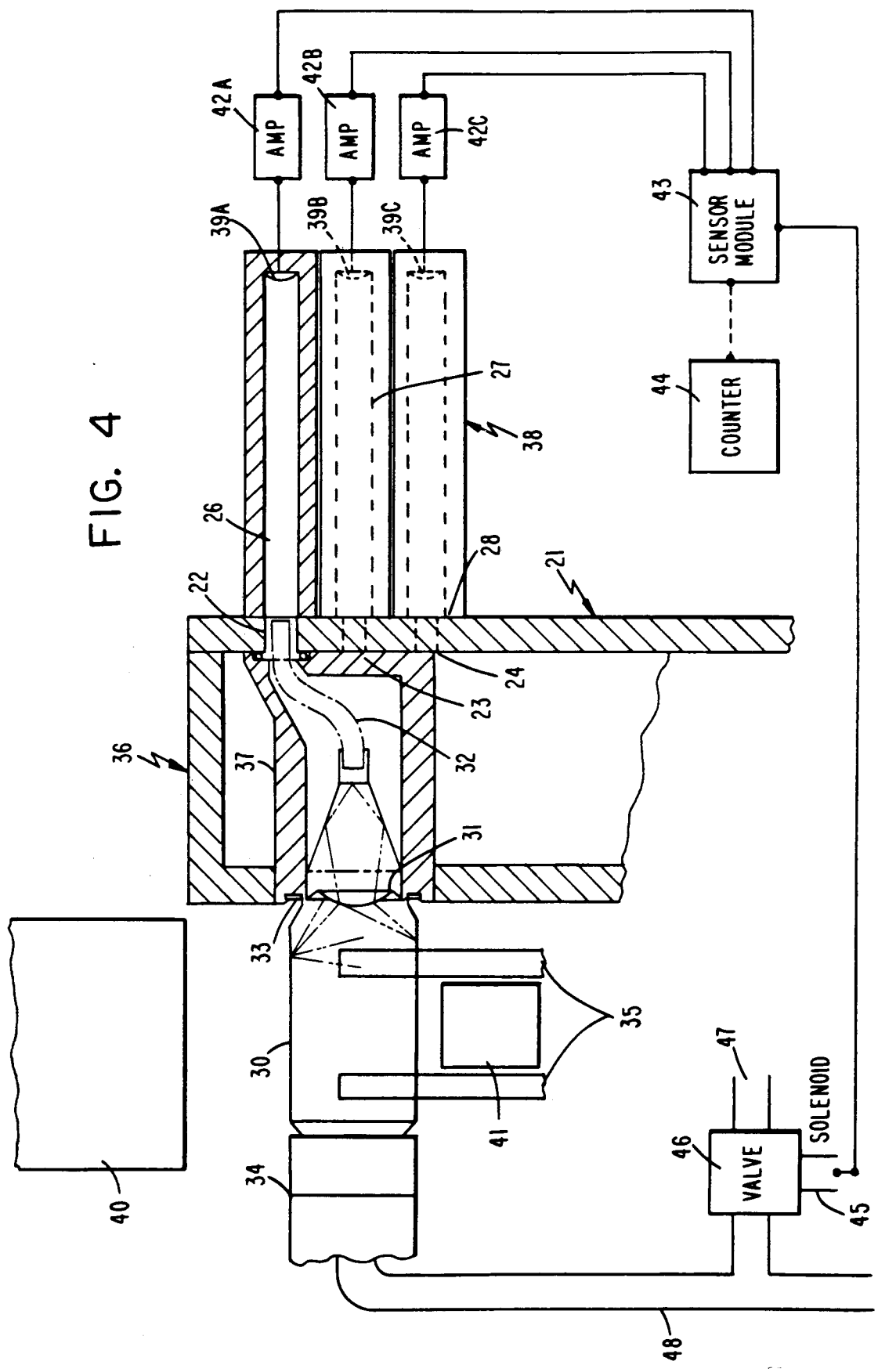
FIG. 4 shows a side sectional view of the inspection area apparatus of FIG. 3 and indicates, schematically, detection signal processing.

The above noted disadvantage is remedied by the preferred embodiment to be described herewith with reference to FIGS. 3 and 4. FIG. 3 shows the relationship at the inspection area among the cans, the disk viewing windows and the sensor apertures. The cans 25 are shown in position for testing. Three stationary detection units are shown having apertures 26, 27 and 28 and are provided for sensing light passing through respective disk windows 22, 23 and 24.

As more fully illustrated in FIG. 4, the can 30 is urged to be in contact with seal 33 at the top flange area by a vacuum actuated base pad 34. Supporting and positioning each can are transparent carrier members 35. Rotating with the carrier is a turret 36, one surface of which comprises disk 21. Rigidly mounted within the turret is a structure 37, including a light gathering lens assembly and fiber optic bundle, for each can position on the carrier. Each structure provides a light seal between the respective lens opening adjacent a can and viewing port in the disk. Stationary sensor housings 38, including apertured channels 26–28 and photomultipliers 39A–39C, are adapted to be in sliding sealed engagement with the disk 21 of the rotating turret.

Light from inside the can is gathered and directed by a lens 31 and fiber optic bundle 32 to one of the small viewing ports 22–23 in the opaque disk 21. The lens focuses all light entering from the container onto the first end of a fiber optic bundle of much smaller diameter. The viewing port, matched in size with the other end of the fiber optic bundle, is therefore much smaller than the diameter of the test can. The lens and fiber optic bundles are well known elements in the optical art.

The above described size relationship permits the use of sensing units having elongated apertured slots which are overlapping and parallel to each other. As shown in FIG. 3, arcuate sensor slots 26, 27 and 28 are positioned at decreasing radial distances from the axis of rotation. Successive viewing ports in the disk 21 are in a path of travel for registration with different sensor apertures. That is, port 22 coincides with slot 26, port 23 coincides with slot 27, port 24 coincides with slot 28 and this sequence is repeated circumferentially about the carrier. Adaptation of this arrangement is attained by bending the respective fiber bundles from a position aligned with the can center at the lens end of the turret to a position aligned with a peripheral point on the can circumference at the disk end of the turret.

In operation, cans are fed to the carrier and held in position by vacuum at the base pad. The carrier and turret rotate and the test can travels into the inspection area wherein it is illuminated within lamp housings 40 and 41. Due to the plurality of sensors and their overlapping relationship described above, the viewing period of each can covers a large extent of the travel path. As shown in FIG. 3, three adjacent test objects are viewed simultaneously.

If a test container has a defect in the form of an opening through the surface, light will be transmitted and directed, via the gathering lens and fiber optic bundle, through the respective viewing port 22-24 and respective sensor slot 26-28. A photosensing element 39A-39C produces a signal in response to the transmitted light, which signal is amplified by the respective amplifier 42A-42C. Sensor module 43 outputs a signal to actuate solenoid 45 to open valve 46 whereupon a controlled amount of compressed air from line 47 is injected into vacuum line 48. The solenoid signal is timed so that the vacuum at the base pad of the defective can is broken to discharge the can into the reject chute. The sensor module also outputs a signal pulse to a counter to keep track of the number of defective cans. The sensor module, vacuum override combination is conventional and used in the aforementioned prior art arrangements.

The above described preferred embodiment extends the viewing time by as much as ten times that possible with the existing prior art devices using a single sensor. The viewing time for each test object can now be as high as 78 mil. sec. at a feed rate of 2000 cans per minute.

Figure 5:
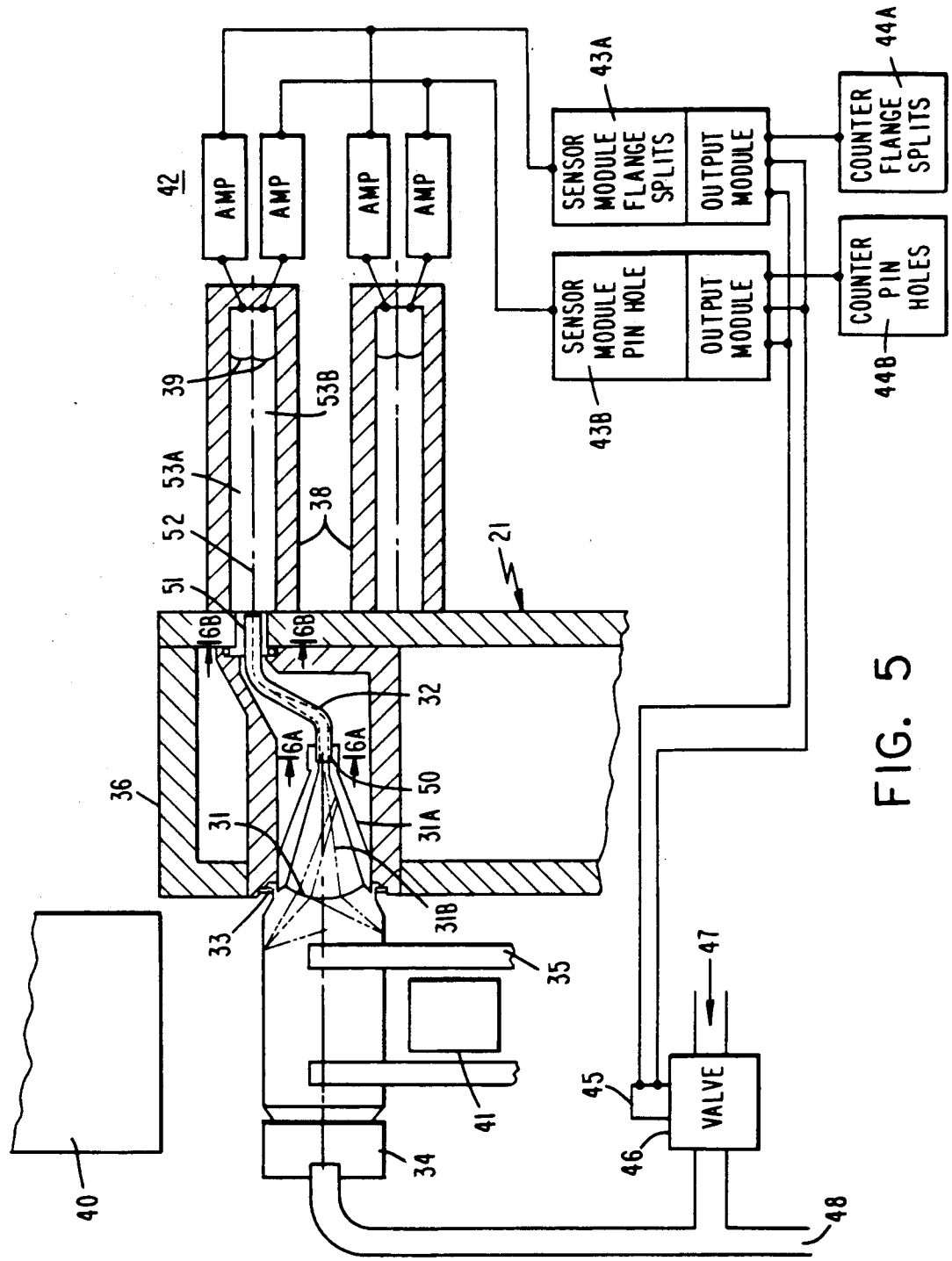
FIG. 5 is a side sectional view similar to FIG. 4 showing a modification of the light directing and sensing apparatus and signal processing.
Figure 6A:
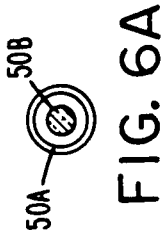
FIG. 6A is a sectional view of an optic fiber bundle taken on line A—A of FIG. 5.
Figure 6B:
FIG. 6B is a sectional view of an optic fiber bundle taken on line B—B of FIG. 6.

FIGS. 5, 6A and 6B show a modification of FIG. 4 wherein provision is made to differentiate between flange leaks and other holes. The gathering lens is split into two concentric areas 31A and 31B to correspond with respective concentric areas on the ends of the fiber optic bundle. The fiber optic bundles are rearranged with the individual fiber locations at the lens end 50 having a different alignment than at the viewing window end 51 of the fibers. This rearrangement is explained in reference to FIGS. 6A and 6B. FIG. 6A shows the fiber ends at the lens side grouped into an outer concentric portion 50A and an inner concentric portion 50B. FIG. 6B shows the fibers at the viewing port side reordered so that the fibers of the outer concentric area form an upper half circle 51A and the fibers of the inner concentric area form a lower half circle 51B.

The sensing unit channels are partitioned by dividers 52 into two subchannels each including a photosensor 39. Light emanating from the upper half circle fibers is directed to the upper subchannel 53A while light from the lower half circle fibers is directed to the lower subchannel 53B. Two of the three sensing units are shown in FIG. 5.

In operation, the outer lens area 31A focuses light received at the peripheral, flange site of the container to the outer concentric fiber ends 50A whereupon the light is directed via the upper half circle fiber ends 51A to subchannel 53A. Light from the center portion of the container is focused by center lens area 31B and is directed to lower subchannel 53B by the fibers having ends at 50B and 51B.

In similar fashion to the signal processing described with respect to FIG. 4, the photosensor signals are amplified and output to sensor modules for counting and rejection of faulty containers. The signals from the upper subchannels indicate faults in the flange areas and are routed to module 43A for counting flange splits; signals from lower subchannels are routed to sensor module 43B for counting surface area pinholes.

There accordingly has been described an apparatus and method for inspecting containers wherein a plurality of sensing units is provided to enable a faster inspection rate as well as a longer viewing time of each container under test. A plurality of containers are inspected simultaneously. Light emanating from peripheral flange areas and central areas of the container are separately directed by respective groups of optic fibers to individual light sensors for respective processing. Flange area defects are thereby distinguishable from side or bottom area defects.

Figure 7:
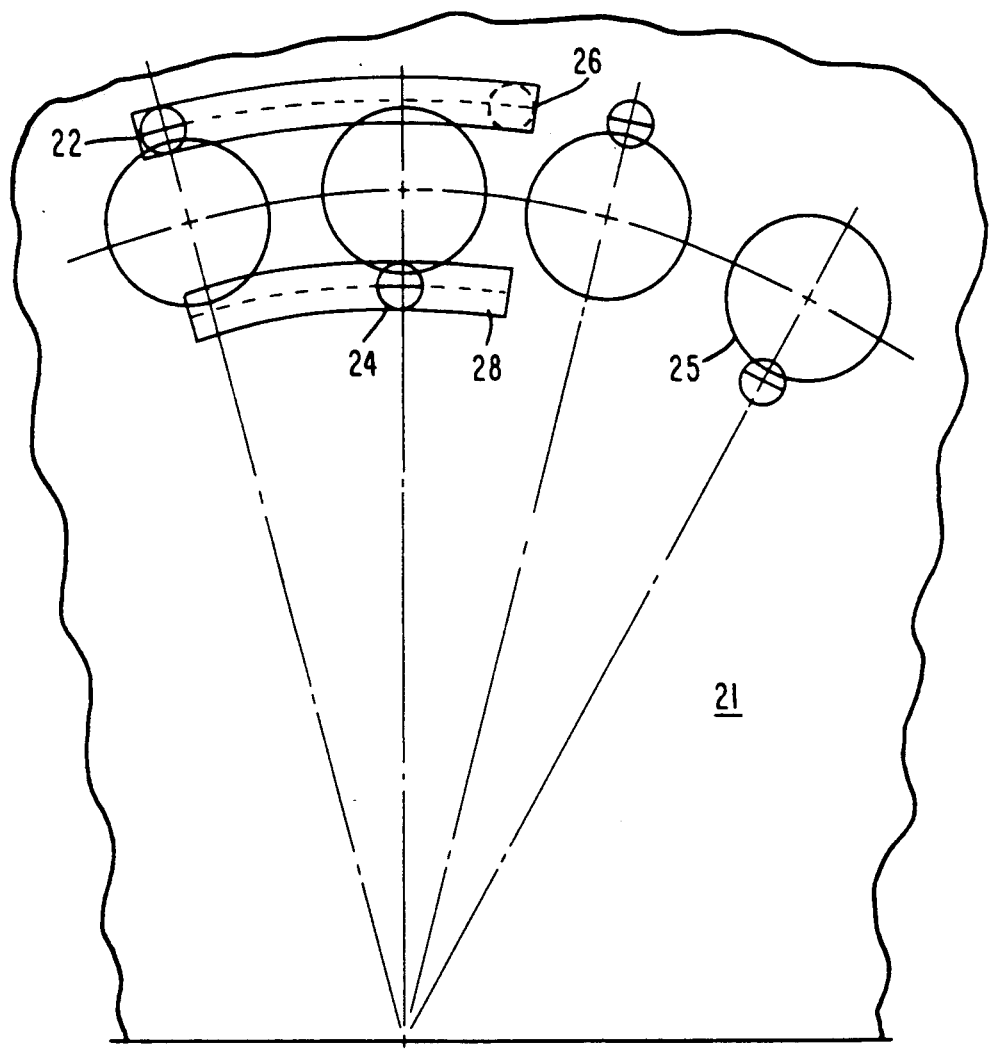
FIG. 7 is a front view of a split fiber embodiment of the invention.

While there has been shown and described the preferred embodiment of FIGS. 3 through 6B, it is to be understood that the invention is capable of various modifications within the scope of the inventive concept as expressed herein. FIG. 7, for example, illustrates an arrangement of two sensors using the split fiber bundle. If it were not important to differentiate the location of the imperfections, the split fiber bundle and subchannel features need not be incorporated and the testing device would count and reject faulty containers in general.

What is claimed is:

1. A light testing apparatus for testing a plurality of container like objects moving in series order along a prescribed path, said path including a portion irradiated by a light source, said apparatus comprising:

a plurality of light conducting means for conducting light, one of said plurality associated respectively with each said object for movement therewith in position to be shielded by said object from said light source; and sensing means responsive to light conducted by said light conducting means, whereby a defect in said object, permitting light transmission from said light source through said defect to said light conducting means, can be determined, wherein said sensing means comprises a light sensing unit, said unit comprising a light sensor disposed within a stationary housing, said housing having an end panel thereof provided with an aperture, said aperture having a slot configuration, said aperture positioned to face said light conducting means.

2. The light testing apparatus of claim 1 wherein said housing further comprises channel means for directing light received through said aperture to said light sensor; said channel means disposed within said housing, said channel means having a first end bounded by said aperture at said panel and a second end accommodating said light sensor.

3. The light testing apparatus of claim 1 wherein said light conducting means comprises a light gathering lens and a fiber optic bundle, said lens focussing light transmitted through said defect, on a first end of said fiber optic bundle.

4. The light testing apparatus of claim 1 wherein said lighting conducting means comprises a light gathering lens and a fiber optic bundle, said lens focussing light transmitted through said defect, on a first end of said fiber optic bundle; and said fiber optic bundle having a second end supported in a surface disposed in a sliding sealed relationship with said sensing means, said second end being in alignment with said slot configuration during movement of said object through said portion irradiated by said light source;

said slot having a length that is greater than twice the dimensional length of said object in the direction of movement.

5. The light testing apparatus of claim 4 wherein said sensing means comprises a plurality of said light sensing units the apertures thereof spaced from each other in parallel to said path of movement and overlapping each other along the direction of said path of movement;

said light conductor means, in said series order of movement, successively being in alignment with a different one of said light sensing units, whereby the testing of adjacent objects is conducted during overlapping time periods.

6. The light testing apparatus of claim 5 wherein said prescribed path of said container like objects is in a radial direction about an axis, said apparatus further comprising:

turret means containing said light conducting means and mounted for rotation with said objects about said axis, said turret means having a first surface perpendicular to said axis, a plurality of said light gathering lenses uniformly disposed in said first surface at a predetermined radial distance from said axis;

said turret means having a second surface parallel to and axially displaced from said first surface, said second surface forming a sliding seal with said stationary housing of said sensing means, said second surface having said second ends of said optic fiber bundles disposed therein.

7. The light testing apparatus of claim 6 wherein said slot configurations of said light sensing units are arcuate in shape and said apertures are positioned at different radial distances from said axis for alignment with corresponding second ends of said optic fiber bundles.

8. The light testing apparatus of claim 7 wherein said turret means comprises an assembly means for rigidly mounting each of said light conducting means, said assembly comprising means for retaining said optic fiber bundles in bent configurations, the second ends of said optic fiber bundles being located at different radial positions in correspondence with said apertures of said light sensing units.

9. The light testing apparatus of claim 5 wherein each of said light sensing units further comprises a divider means for forming two subchannels each directing received light to a corresponding light sensor contained therein;

said fiber optic bundle comprises a center concentric area and an outer concentric area at said first end, light received from a central area of said object being gathered by the optic fibers in the center concentric area, light received from a peripheral area of said object being gathered by the optic fibers in the outer concentric area;

said second end of said fiber optic bundle comprises a first half circle cross section including said fibers of said center concentric area of said first end a second half circle cross section including said fibers of said outer concentric area of said first end; and means for aligning said first half circle with one of said subchannels and said second half circle with the other of said subchannels, whereby a defect in said peripheral area or in said central area of said object can be identified.

10. The light testing apparatus of claim 8 where each of said light sensing units further comprises a divider means for forming two subchannels each of said subchannels directing received light to a corresponding light sensor contained therein;

said fiber optic bundle comprises a center concentric area and an outer concentric area at said first end, light received from a central area of said object being gathered by the optic fibers in the center concentric area, light received from a peripheral area of said object being gathered by the optic fibers in the outer concentric area;

said second end of said fiber optic bundle comprises a first half circle cross section including said fibers of said center concentric area of said first end a second half circle cross section including said fibers of said outer concentric area of said first end; and means for aligning said first half circle with one of said subchannels and said second half circle with the other of said subchannels, whereby a defect in said peripheral area or in said central area of said object can be identified.

11. In an apparatus for automatically inspecting containers for openings including stationary light emitting means spaced from photosensitive detecting means, rotatable carrier means for moving said containers between said light emitting means and said detecting means, said carrier means having a plurality of container carrying positions radially disposed about an axis of rotation, shielding means comprising an opaque plate having a window facing a container top opening portion at each position, said detecting means responsive to light from said light emitting means passing through any hole in a container wall and a path including the container top opening and plate window whereby a defect in the container can be determined, the improvement wherein:

said light detecting means comprises a plurality of light sensing units each comprising a light sensor disposed within a stationary housing, said housing having an end panel thereof provided with an aperture having an arcuate slot configuration, the length of said slot being significantly greater than the diameter of any of said containers, said sensing unit responsive sequentially to detect different containers.

12. The apparatus of claim 11 further comprising light directing means, integral with and rotatable with said carrier means, said light directing means comprising a lens and fiber optic bundle for each of said container carrying positions, said lens adjacent said container position for directing light received through a container opening to a first end of said fiber optic bundle.

13. The apparatus of claim 12 wherein said aperture is positioned to face a second end of a corresponding fiber optic bundle and said housing further comprises channel means disposed therewithin for directing light received through said aperture to said light sensor, said channel having a first end bounded by said aperture at said panel and a second end accommodating said light sensor.

14. The apparatus of claim 13 wherein the apertures of the light sensing units are spaced from each other in parallel and overlapping relationship along the radial direction of movement of the containers, the second end of said fiber optic bundle for each said container carrying position successively being in alignment with a different one of said light sensing units, whereby testing of adjacent objects is conducted during overlapping time periods.

15. The apparatus of claim 13 wherein each of said light sensing units further comprises a divider means for forming two subchannels each directing received light to a corresponding light sensor contained therein;
   said fiber optic bundle comprises a center concentric area and an outer concentric area at said first end, light received from a central area of said object being gathered by the optic fibers in the center concentric area, light received from a peripheral area of said object being gathered by the optic fibers in the outer concentric area;
   said second end of said fiber optic bundle comprises a first half circle cross section including said fibers of said center concentric area of said first end a second half circle cross section including said fibers of said outer concentric area of said first end; and
   means for aligning said first half circle with one of said subchannels and said second half circle with the other of said subchannels, whereby a defect in said peripheral area or in said central area of said object can be identified.

16. The apparatus of claim 11 wherein said light detecting means comprises two light sensing units and each window in said shielding means is chord shaped, successive windows being disposed opposite on alternating sides of the center of the container top portions whereby inspection of adjacent containers is conducted during overlapping time periods.

17. In a container inspection apparatus including a stationary light source spaced from a photosensitive detector, a carrier having a plurality of container carrying positions and an opaque plate having a window facing a container top opening portion at each position, a testing method comprising:
   feeding containers at high speed to said carrier, moving said carrier to place said containers successively in a prescribed path between said light source and said detector to illuminate the exterior surfaces of said containers by said light source,
   shielding said detector from unwanted light, and
   simultaneously inspecting adjacent containers for light transmitted from said light source through openings in said surfaces,
   whereby faulty containers can be determined.

18. The method of claim 17 wherein said inspecting step comprises:
   directing light from successive adjacent containers along spaced parallel paths, each path being in registration with a respective photosensor.

* * * * *